(12) United States Patent
Gless, Jr. et al.

(10) Patent No.: US 9,617,265 B2
(45) Date of Patent: Apr. 11, 2017

(54) NORIBOGAINE SALT ANSOLVATES

(71) Applicant: DemeRx, Inc., Fort Lauderdale, FL (US)

(72) Inventors: Richard D. Gless, Jr., Oakland, CA (US); William C. Schinzer, Portage, MI (US)

(73) Assignee: DEMERX, INC., Fort Lauderdale, FL (US)

( * ) Notice: Subject to any disclaimer, the term of this patent is extended or adjusted under 35 U.S.C. 154(b) by 0 days.

(21) Appl. No.: 14/720,753

(22) Filed: May 23, 2015

(65) Prior Publication Data
US 2016/0108043 A1 Apr. 21, 2016

Related U.S. Application Data

(63) Continuation of application No. 13/619,520, filed on Sep. 14, 2012, now Pat. No. 9,040,520.

(60) Provisional application No. 61/535,300, filed on Sep. 15, 2011.

(51) Int. Cl.
*A61K 31/55* (2006.01)
*C07D 471/22* (2006.01)

(52) U.S. Cl.
CPC ............ *C07D 471/22* (2013.01); *A61K 31/55* (2013.01)

(58) Field of Classification Search
CPC .............................. C07D 471/22; A61K 31/55
See application file for complete search history.

(56) References Cited

U.S. PATENT DOCUMENTS

| | | | |
|---|---|---|---|
| 2,813,873 A | 11/1957 | Janot et al. | |
| 5,591,738 A | 1/1997 | Lotsof | |
| 6,348,456 B1 | 2/2002 | Mash et al. | |
| 7,220,737 B1 * | 5/2007 | Mash ................... | A61K 31/397 514/210.05 |
| 7,754,710 B2 | 7/2010 | Mash | |
| 2004/0102638 A1 | 5/2004 | Russell et al. | |
| 2009/0186878 A1 | 7/2009 | Morris et al. | |
| 2010/0311725 A1 | 12/2010 | Mash | |

FOREIGN PATENT DOCUMENTS

| | | |
|---|---|---|
| EP | 2 481 740 A1 | 8/2012 |
| EP | 2 755 658 | 7/2014 |
| GB | 0 789 870 A | 1/1958 |
| WO | WO-2012/012764 A1 | 1/2012 |
| WO | WO-2013/040471 | 3/2013 |

OTHER PUBLICATIONS

Thomas et al ( Acta anaesthesiological Scandinavica, 1994, 38(1), 63-69).*
Bartlett et al (JACS, 1958, 80, 126-136).*
Bartlett, et al. "The Alkaloids of Tabernanthe iboga. Part IV. The Structures of Ibogamine, Ibogaine, Tabernanthine and Voacangine." Journal of the American Chemical Society, 80, 1958, pp. 126-136.
First Examination Report in New Zealand Patent Application No. 620948, dated Dec. 17, 2014.
International Search Report and Written Opinion dated Feb. 25, 2013 in related PCT Application No. PCT/US2010/055597.
Office Action on Thai Application 1401001302, mailed Jun. 9, 2015.
Substantive Examination Report issued on Philippines Application 1/2014/500589, mailed Jul. 31, 2015.
Supplementary Extended European Search Report dated Feb. 18, 2015 in EP Patent Application No. 12832208.8.
Thomas, et al., "Importance of modes of accupuncture in the treatment of chronic noncieceptive low back pain" Acta anaesthesiological Scandinavica, 38(1),63-69) (1994).
Search Report issued on Vietnam Application 1-2014-00698, mailed Jan. 27, 2016.
Second Office Action issued on Chinese Application 201280039971.6, mailed Feb. 22, 2016, English Translation provided.

* cited by examiner

*Primary Examiner* — Jason Sims
*Assistant Examiner* — Ibrahim D Bori
(74) *Attorney, Agent, or Firm* — Foley & Lardner LLP

(57) ABSTRACT

Stable noribogaine salt ansolvates are useful for preparing pharmaceutical compositions and for alleviating nociceptive pain in a patient. Such ansolvates can be prepared by slurrying solvated forms, preferably MeOH solvated noribogaine hydrochloride in EtOH/water.

5 Claims, 12 Drawing Sheets

NORIBOGAINE SALT ANSOLVATES

CROSS REFERENCE TO RELATED APPLICATION

This application is continuation of and claims priority to U.S. application Ser. No. 13/619,520, filed on Sep. 14, 2014, entitled "Noribogaine Salt Ansolvates," which claims the benefit under 35 U.S.C. 119(e) of U.S. Provisional Application Ser. No. 61/535,300, filed Sep. 15, 2011, which is hereby incorporated by reference into this application in its entirety.

FIELD OF THE INVENTION

This invention relates to stable solid forms of noribogaine salts and pharmaceutical uses thereof. In one embodiment, the stable salts are crystalline ansolvates. In another embodiment, the stable salts are amorphous ansolvates.

STATE OF THE ART

Noribogaine is a compound of formula:

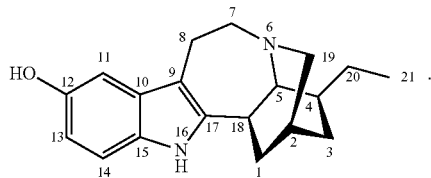

Noribogaine and its pharmaceutically acceptable salts, such as for example the hydrochloride salt, have recently received significant attention as a non-addictive alkaloid useful in treating drug dependency (U.S. Pat. No. 6,348,456) and as a potent analgesic (U.S. Pat. Nos. 7,220,737 and 7,754,710). Each of these patents are incorporated herein by reference in their entirety.

When used for treating humans, an orally delivered, solid formulations of therapeutic agent preferably need to meet certain criteria. For a tablet composition of the therapeutic agent, the tablet must be compressible and shear-stable, where the agent should be compatible with one or more excipients and not undergo morphological change during storage or manufacture. Likewise, the therapeutic agent in a tablet or capsule must be dense enough to pack enough of the agent with the understanding that smaller tablets or capsules are deemed to be more easily ingested than larger ones.

One of the critical factors for processing such a therapeutic agent is the packing of the agent in its crystal lattice. Accordingly, the selection of a polymorph from a manufacturing perspective is very critical. The therapeutic agent must also be sufficiently stable, must retain its polymorphic form during manufacture of a tablet or a capsule dosage form, and must not degrade during a normal shelf-life storage. Each of these criteria is critical to ensure that unacceptable by-products are not formed. Very few polymorphic forms of an active agent satisfy all of these criteria so as to be suitable for use as the active ingredient in a orally delivered, solid formulation of the therapeutic agent.

As to noribogaine hydrochloride a number of crystal polymorphs in the form of a solvate have been identified. These solvated crystalline polymorphs unfortunately lack one or more of the characteristics defined above to be suitable as an active in a pharmaceutical composition.

Accordingly, there is a need to define one or more forms of noribogaine hydrochloride which meet each of the above criteria.

SUMMARY

It has now been unexpectedly discovered that certain ansolvates of noribogaine salts are substantially more stable and can maintain their polymorphic forms during manufacture and storage and have a suitable density to allow for facile manufacture of capsules and/or tablets. These certain ansolvates are characterized by either a crystalline or amorphous structure.

In one embodiment, the ansolvates of this invention preferably have a density that is at least 3% and up to 20%, or more preferably at least 5% and up to 15%, greater than the density of a solvated crystalline hydrochloride salt of noribogaine.

In another embodiment, ansolvates are crystalline ansolvates of noribogaine hydrochloride having a by a unit cell volume of less than about 1850 cubic angstrom, preferably less than about 1800 cubic angstrom, more preferably, less than about 1750 cubic angstrom, or most preferably less than 1700±2% cubic angstrom. For a crystalline ansolvate polymorph, it is contemplated that a smaller unit cell volume correlates with a higher density of that polymorph.

Such stable crystalline ansolvate salts include the hydrochloride salt, the sulfate salt, and the tosylate salt, each of which demonstrate superior stability and other superior physicochemical properties compared to solvated crystalline forms, which include methanol or water as the solvent. Preferably, the salt is a hydrochloride salt.

The crystalline ansolvate polymorphs of this invention provide several advantages including enhanced heat stability as compared to solvated forms. Also, its density is increased compared to ansolvates created by desolvation of solvated polymorphs of noribogaine hydrochloride. In the latter case, the loss of solvent in the solvated polymorph leads to spatial gaps (holes) in the crystal structure which render it less dense and potentially capable of undergoing an undesirable form conversion during high-pressure manipulations of tableting and formulating. The denser ansolvate polymorphs of this invention provide more compact and smaller tablets than solvated polymorphs for tableting while using the same amount of a noribogaine salt.

As used herein, the term "stable" or "stability" of a polymorph refers to polymorphic and/or chemical stability at about 25° C., and preferably at about 40° C. for at least 1 day, preferably for at least a week, and more preferably for several months. More preferably, the ansolvate polymorphs of this invention are stable under the aforementioned conditions and at about 75% relative humidity (RH), yet more preferably at about 97% RH. Still more preferably, stability refers to stability for at least 1 day, preferably for at least a week, at about 25° C. and about 75% RH, more preferably at about 40° C. and 75% relative humidity (RH), and still more preferably at about 40° C. and about 97% RH. A "stable" polymorph does not undergo polymorphic transformation when exposed to moisture and or heating, for example, up to about 40° C. In addition, chemical/polymorphic stability can be further measured by no observable change in one or more of, preferably, two of, more preferably three of, and most preferably all of, XRPD, TGA, DVS, IR, and $^1$H-NMR of the solid form. However, the stability of compounds somewhat less stable under humidity or moisture exposure can be enhanced by adding desiccants well known to the skilled artisan.

Surprisingly, the corresponding crystalline solvated salts of noribogaine are not stable and/or are not polymorphically pure, nor are these crystalline noribogaine forms obtained by desolvating these solvates. Such unstable desolvated forms are referred to herein as "unstable porous crystalline noribogaine ansolvate salts" as removal of the solvate results in the formation of pores within the crystalline structure. As used herein, stable crystalline ansolvate noribogaine salts do not include "unstable porous crystalline noribogaine ansolvate salts."

Accordingly, in one aspect, this invention provides for stable ansolvate noribogaine salts and, in particular, stable crystalline ansolvate salt. In one embodiment, the salt is a pharmaceutically acceptable salt. In one embodiment, the salt is an ansolvate of the hydrochloride salt of noribogaine (NI.HCl, Form A or Form I). In another embodiment, the salt is an ansolvate of the tosylate salt of noribogaine (NI.TsOH, Form B). In another embodiment, the salt is an ansolvate sulfate salt (NI.H$_2$SO$_4$, Form D).

In one embodiment, the crystalline stable ansolvate noribogaine hydrochloride shows substantially no weight loss at temperatures under 300° C. in its thermogravimetric analysis (TGA) thermogram evidencing the lack of solvent in the crystal structure. In another embodiment, the crystalline stable ansolvate noribogaine hydrochloride has a density that is at least 3% and up to 20%, or preferably at least 5% and up to 15% greater than the density of a solvated crystalline hydrochloride salt of noribogaine. In another embodiment, the crystalline stable ansolvate noribogaine hydrochloride has a unit cell volume of less than about 1850 cubic angstrom, preferably less than about 1800 cubic angstrom, more preferably, less than about 1750 cubic angstrom, or most preferably less than 1700±2% cubic angstrom.

In another embodiment, this invention provides a solvated crystalline noribogaine hydrochloride polymorph characterized by about 4% weight loss at temperatures under 125° C., preferably at temperatures ranging from 27° C. to 125° C. in its TGA thermogram. In another embodiment, the solvated crystalline noribogaine hydrochloride polymorph is characterized by at least one X-ray powder diffraction peak (Cu Kα radiation) selected from 9.7, 10.2, 12.0, 13.3, 13.7, 16.0, 16.3, 17.7, 18.0, 19.4, 21.4, 22.1, 22.8, 24.4, 25.1° 2θ (each ±0.2° 2θ). In another embodiment, such a solvated polymorph is characterized by the X-ray diffraction pattern as substantially shown in the two top panels of FIG. 4.

It has also been discovered that a solvated hydrochloride polymorph of noribogaine obtained from MeOH is surprisingly converted to a pure, ansolvate polymorph of noribogaine hydrochloride upon stirring in EtOH/water, e.g., 9:1 EtOH/water. Accordingly, also provided herein is a process of preparing a noribogaine hydrochloride ansolvate comprising slurrying a noribogaine solvate, preferably, one obtained from MeOH, in EtOH/water. It is noted that solvated hydrochloride polymorph of noribogaine obtained from methanol is an intermediate for the preparation of a polymorph of this invention and, accordingly, is part of the invention as claimed.

The table below demonstrates the superior moisture stability of the ansolvate, hydrochloride Form A polymorph.

TABLE 1

| Salt/Form | Stoichiometry | Approx. Aqueous Solubility | RH Stability |
|---|---|---|---|
| HCl, Form A | 1:1 salt | 1-4 mg/mL | About 97% RH/RT: no form change after 7 days. |
| Tosylate, Form B | Likely 1:1 salt | 3 mg/mL | About 75% RH/RT: no deliquescence after 1 day. About 97% RH/RT: deliquesced after 1 day. |
| Phosphate, Form C | 1:1 salt | 23 mg/mL | About 75% RH/RT: no deliquescence after 1 day. About 97% RH/RT and about 75% RH/about 41° C.: no deliquescence and no form change after 7 days. |
| Sulfate, Form D | 1:1 salt | >80 mg/mL | About 75% RH/RT: no deliquescence. About 97% RH/RT: deliquesced after 1 day. About 75% RH/about 41° C.: no deliquescence and no form change after 7 days. |

The superior polymorphic and thermal stability of Form A and the other polymorphic forms are also evidenced by comparing the XRPD patterns of FIGS. 3 and 5, and the thermograms of FIGS. 1 and 2 and those of FIGS. 6 and 10-12.

To determine the effect of relative humidity, weighed amounts of relevant noribogaine starting materials were transferred to vials, which were then uncapped and placed inside a jar containing a saturated aqueous salt solution: sodium chloride was used for ~75% RH and potassium sulfate for ~97% RH. Relative humidity stressing experiments were conducted at ambient and elevated temperatures for given durations.

Two other moisture absorbing, unstable, polymorphs of noribogaine hydrochloride, Forms F and G, which had mutually similar XRPD patterns were also identified. Form G was isolated from a slurry of Form A in MeOH at ambient temperature. Material G likely contains MeOH and water, and Form F (or Form II) is likely hydrated. After drying, material G exhibited 7.95% gravimetric weight loss and converted to Form A, as characterized by XRPD. Form F showed 4.1% gravimetric weight loss indicating the presence of solvent in the polymorph and is converted to Form A as characterized by XRPD. A sharp weight loss at ~312° C. indicated likely decomposition. Both Forms G and F are contemplated to readily pick up moisture from the atmosphere.

In another embodiment, the crystalline noribogaine hydrochloride ansolvate is characterized by the onset of an endothermic peak at approximately 308° C. with a peak as measured by differential scanning calorimetry at approximately 315° C. In another embodiment, the crystalline noribogaine hydrochloride ansolvate is characterized by the substantial absence of thermal events at temperatures below the endothermic peak at about 308±° C. as measured by differential scanning calorimetry. In another embodiment, the crystalline noribogaine hydrochloride ansolvate is characterized by a DSC or a TGA thermogram substantially similar to that of FIG. 1. In another embodiment, the crystalline noribogaine hydrochloride ansolvate is characterized by a DVS pattern substantially similar to that of FIG. 2. In another embodiment, the crystalline noribogaine hydrochloride ansolvate is characterized by at least one, at least two, or at least three X-ray powder diffraction peaks (Cu Kα radiation) selected from 11.6°, 12.1°, 13.5°, 13.9°, 14.9°, 15.7°, 17.1, 17.9°, 18.3°, 19.8°, 20.8°, 21.0°, 21.9°, 22.8°, 23.3°, 24.9°, 25.9°, 26.4, 29.3°, and 29.8° 2θ (each ±0.2° 2θ). In another embodiment, the crystalline noribogaine hydrochloride ansolvate is characterized by an X-ray powder diffraction pattern (Cu Kα radiation) substantially similar to that of FIG. 3.

In another embodiment, the crystalline NI.H$_3$PO$_4$ is characterized by an XRPD pattern substantially similar to that of any one of patterns in FIG. 5. In another embodiment, the crystalline NI.H$_3$PO$_4$ is characterized by a DSC or a TGA thermogram substantially similar to that of FIG. 6.

In another embodiment, the crystalline noribogaine sulfate ansolvate (NI.H$_2$SO$_4$) is characterized by at least one, at least two, or at least three X-ray powder diffraction peaks (Cu Kα radiation) selected from 8.5°, 11.4°, 12.0°, 15.4°, 16.6°, 17.2°, and 18.3° 2θ (each ±0.2° 2θ). In another embodiment, the crystalline noribogaine sulfate ansolvate (NI.H$_2$SO$_4$) is characterized by an X-ray powder diffraction pattern (Cu Kα radiation) substantially similar to that of FIG. 8. In another embodiment, the crystalline NI.H$_2$SO$_4$ is characterized by a DSC or a TGA thermogram similar to that of FIG. 9. In another embodiment, the crystalline NI.H$_2$SO$_4$ is characterized by a DVS pattern similar to that of FIG. 10.

In one of its composition embodiments, this invention provides a composition comprising the stable, crystalline noribogaine salt ansolvates provided herein, and preferably the Form A ansolvate. In another of its composition embodiments, this invention provides a pharmaceutical composition comprising a pharmaceutically acceptable excipient and the stable crystalline noribogaine salt ansolvates provided herein, preferably the Form A ansolvate.

In another of its composition embodiments, this invention provides a kit comprising: the ansolvates provided herein, preferably the sulfate and the tosylate Forms B and D; or a composition comprising the ansolvate provided herein, preferably the sulfate and the tosylate Forms B and D; or a pharmaceutical composition comprising the ansolvate provided herein, preferably the sulfate and the tosylate Forms B and D; and a pharmaceutically acceptable excipient, and a desiccant. Various suitable desiccants appropriate for use in this kit is well known to the skilled artisan.

In one of its method embodiments, this invention provides a method of storing the ansolvates provided herein, preferably the tosylate and sulfate Forms B and D, comprising storing the ansolvate crystals or a composition or a pharmaceutical composition comprising the ansolvate crystals, in an anhydrous environment, preferably in the presence of nitrogen or argon, and more preferably in the presence of a desiccant.

In one of its method embodiments, this invention provides a method of treating a patient to alleviate nociceptive pain in the absence of the treatment of drug dependence or drug abuse and in the absence of any concomitant opioid analgesic therapy, comprising: administering systemically to said patient a pharmaceutical composition comprising an effective amount of the crystalline noribogaine salt, preferably an ansolvate salt as provided here, or the compositions, including the pharmaceutically acceptable compositions, provided here, to said patient effective to reduce or eliminate said nociceptive pain in said patient. As used herein, opioids refer to compounds that show its pharmacological effect by binding to opioid receptors, and include natural (such as the opiates) and synthetic compounds well known to the skilled artisan. In all of such treatments, the dosing of crystalline noribogaine salt to the treated patient is already disclosed in the art. See, for example, U.S. Pat. Nos. 6,348,456, 7,220, 737, and 7,754,710, each of these patents are incorporated herein by reference in their entirety.

DETAILED DESCRIPTION OF THE INVENTION

Figure 1:
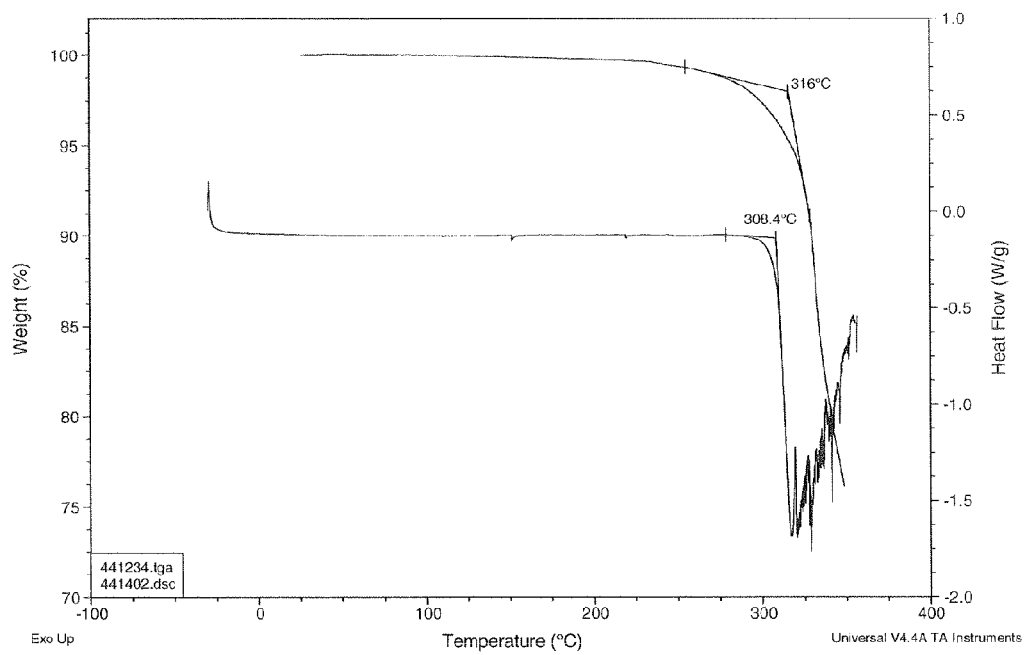
FIG. 1 is an overlay of a differential scanning calorimetry (DSC) and a thermogravimetric analysis (TGA) patterns of noribogaine hydrochloride ansolvate Form A.

As noted above, this invention is directed, in part, to a stable crystalline ansolvates of noribogaine salts and, in particular, to the hydrochloride salt. However, prior to discussing this invention in further detail, the following terms will be defined.

Definitions

As used herein, the following terms have the following meanings

The singular forms "a," "an," and "the" and the like include plural referents unless the context clearly dictates otherwise. Thus, for example, reference to "a compound" includes both a single compound and a plurality of different compounds.

The term "about" when used before a numerical designation, e.g., temperature, time, amount, and concentration, including a range, indicates approximations which may vary by ±10%, ±5% or ±1%.

"Administration" refers to introducing an agent into a patient. A therapeutic amount can be administered, which can be determined by the treating physician or the like. An oral route of administration is preferred. The related terms and phrases "administering" and "administration of", when used in connection with a compound or pharmaceutical composition (and grammatical equivalents) refer both to direct administration, which may be administration to a patient by a medical professional or by self-administration by the patient, and/or to indirect administration, which may be the act of prescribing a drug. For example, a physician who instructs a patient to self-administer a drug and/or provides a patient with a prescription for a drug is administering the drug to the patient. In any event, administration entails delivery to the patient of the drug.

The "crystalline ansolvate" of noribogaine hydrochloride is a crystalline solid form of a noribogaine salt, such as, e.g., the crystalline Form A or D. Such a crystal lattice is substantially free of solvents of crystallization. However, any solvent present is not included in the crystal lattice and is randomly distributed outside the crystal lattice. Therefore, ansolvate crystals in bulk may contain, outside the crystal lattice, small amounts of one or more solvents, such as the solvents used in its synthesis or crystallization. As used above, "substantially free of" and "small amounts," refers to the presence of solvents preferably less that 10,000 parts per million (ppm), or more preferably, less than 5000 ppm.

"Comprising" or "comprises" is intended to mean that the compositions and methods include the recited elements, but not exclude others. "Consisting essentially of" when used to define compositions and methods, shall mean excluding other elements of any essential significance to the combination for the stated purpose. Thus, a composition or a method consisting essentially of the elements as defined herein would not exclude, respectively, other materials or steps that do not materially affect the basic and novel characteristic(s) of the claimed composition or method. "Consisting of" shall mean excluding more than trace elements of other ingredients and substantial method steps. Embodiments defined by each of these transition terms are within the scope of this invention.

"Pharmaceutically acceptable" refers to non-toxic material suitable for in vivo and preferably human administration.

"Therapeutically effective amount" or "therapeutic amount" refers to an amount of a drug or an agent that when administered to a patient suffering from a condition, will have the intended therapeutic effect, e.g., alleviation, amelioration, palliation or elimination of one or more manifestations of the condition in the patient. The therapeutically effective amount will vary depending upon the subject and the condition being treated, the weight and age of the subject, the severity of the condition, the particular composition or excipient chosen, the dosing regimen to be followed, timing of administration, the manner of administration and the like, all of which can be determined readily by one of ordinary skill in the art. The full therapeutic effect does not necessarily occur by administration of one dose, and may occur only after administration of a series of doses. Thus, a therapeutically effective amount may be administered in one or more administrations. For example, and without limitation, a therapeutically effective amount of an agent, in the context of alleviating nociceptive pain, refers to an amount of the agent that reduce or eliminate one or more manifestations of the nociceptive pain in the patient.

"Treatment", "treating", and "treat" are defined as acting upon a disease, disorder, or condition with an agent to reduce or ameliorate the harmful or any other undesired effects of the disease, disorder, or condition and/or its symptoms and produce beneficial or desired clinical results. Treatment, as used herein, covers the treatment of a human patient, and includes: (a) reducing the risk of occurrence of the condition in a patient determined to be predisposed to the disease but not yet diagnosed as having the condition, (b) impeding the development of the condition, and/or (c) relieving the condition, i.e., causing regression of the condition and/or relieving one or more symptoms of the condition. For purposes of this invention, beneficial or desired clinical results include, but are not limited to, reducing or eliminating nociceptive pain.

Preparing and Characterizing the Noribogaine Polymorphs

The noribogaine hydrochloride ansolvate Form A is prepared by reacting noribogaine free base with hydrochloric acid in a variety of solvents, or by crystallizing the hydrochloride from a variety of solvents as tabulated in the Examples section below. Upon slow evaporation of noribogaine hydrochloride from a methanol slurry over 7 days, a Form G crystal different from Form A is obtained. See top panel, FIG. 4. Form G or F crystals are converted to form A ansolvates upon stirring in EtOH-water, as described herein below.

The Form A crystals were indexed as shown below. Successful indexing of the XRPD patterns indicates that sample is composed primarily of a single crystalline phase.

Noribogaine Hydrochloride Form A

| Bravais type | Primitive orthorhombic |
|---|---|
| a [Å] | 8.943 |
| b [Å] | 13.019 |
| c [Å] | 14.584 |
| α [deg] | 90 |
| β [deg] | 90 |
| γ [deg] | 90 |
| Volume [Å$^3$/cell] | 1,698.1 |
| Chiral Contents? | Chiral |
| Extinction Symbol | P 21 21 21 |
| Space Group(s) | P 21 21 21 (19) |

Figure 2:
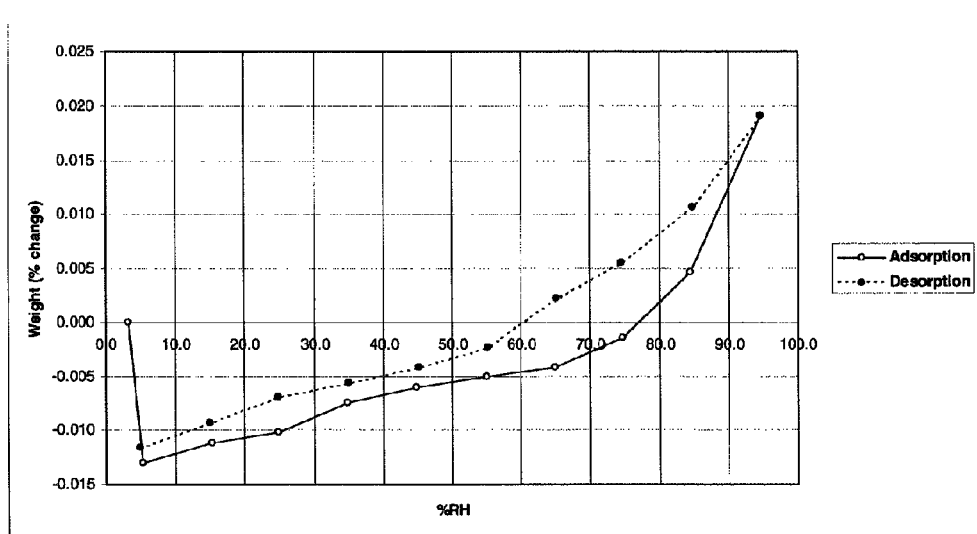
FIG. 2 shows dynamic vapor sorption (DVS) curves for noribogaine hydrochloride ansolvate Form A.
Figure 11:
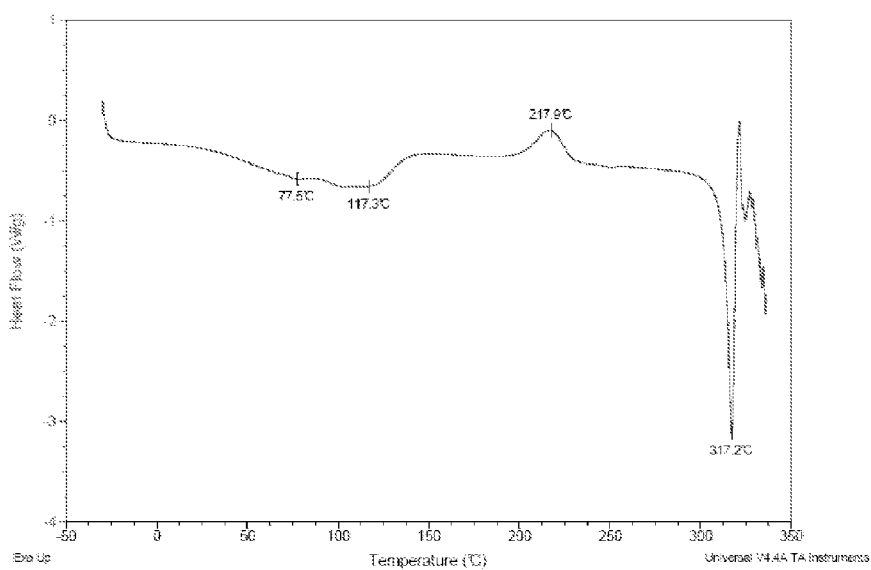
FIG. 11 shows a DSC pattern of noribogaine hydrochloride Form F.
Figure 12:
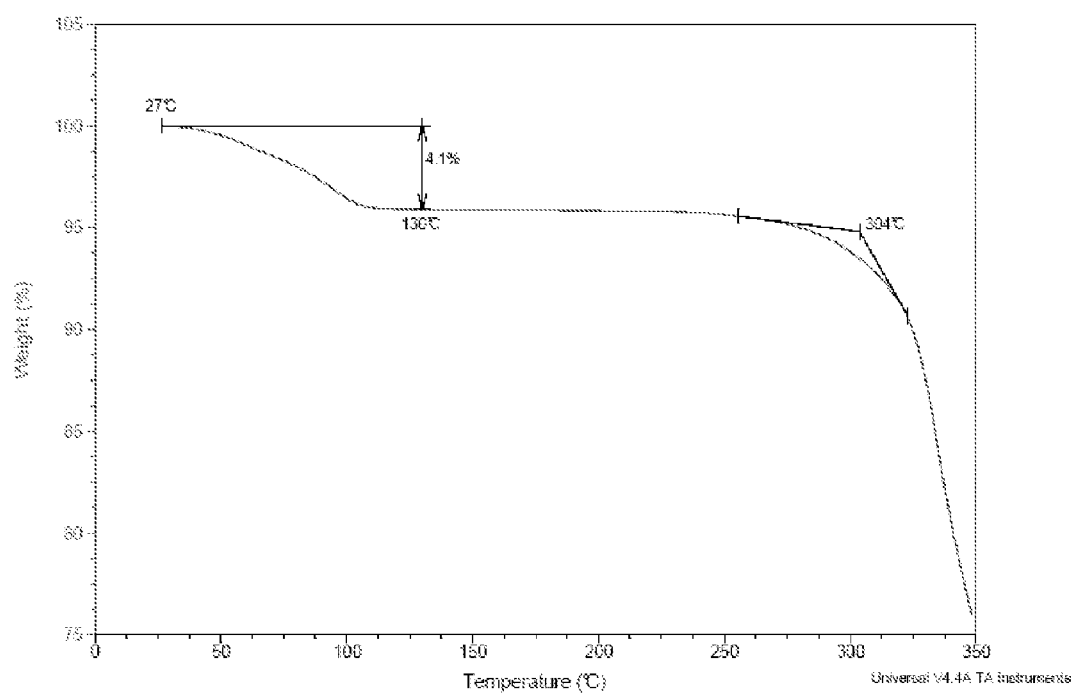
FIG. 12 shows a TGA pattern of noribogaine hydrochloride Form F.

Thermogravimetric data for Form A crystals show negligible weight loss prior to ~316° C. at which point a sharp weight loss is observed, indicating probable decomposition (FIG. 1). The DSC thermogram shows likely simultaneous melting and decomposition above approximately 300° C., consistent with the TGA data. Form A crystals, when characterized by DSC, did not show one or more broad endotherms related to desolvation, as observed, for Form F solids (see, FIG. 11). The compound exhibited virtually no hygroscopicity by dynamic vapor sorption (DVS), showing weight gain/loss of only approximately 0.03% between 5 and 95% relative humidity (FIG. 2).

The approximate ambient-temperature solubilities of noribogaine hydrochloride Form A were measured in a variety of solvents and solvent mixtures using the solvent addition method (Table 2). The material exhibited low solubility in most of the solvents tested, and was more soluble in a number of organic-aqueous mixtures, HFIPA, MeOH, and TFE.

Samples from the slurry and accelerated stability experiments of Form C exhibited a minor amount of peak shifting by XRPD, indicating a family of XRPD patterns. The XRPD patterns were successfully indexed as shown below.

| Bravais type | Triclinic |
|---|---|
| a [Å] | 9.190 |
| b [Å] | 10.234 |
| c [Å] | 11.009 |
| α [deg] | 75.45 |
| β [deg] | 73.16 |
| γ [deg] | 78.38 |
| Volume [Å$^3$/cell] | 949.9 |
| Chiral Contents? | Chiral |
| Extinction Symbol | P - |
| Space Group(s) | P 1 (1) |

For another slightly peak shifted form of Form C, the following indexing was obtained.

| Bravais type | Triclinic |
|---|---|
| a [Å] | 9.226 |
| b [Å] | 10.212 |
| c [Å] | 11.022 |
| α [deg] | 75.48 |
| β [deg] | 72.65 |
| γ [deg] | 78.02 |
| Volume [Å³/cell] | 949.6 |
| Chiral Contents? | Chiral |
| Extinction Symbol | P - |
| Space Group(s) | P 1 (1) |

Figure 6:
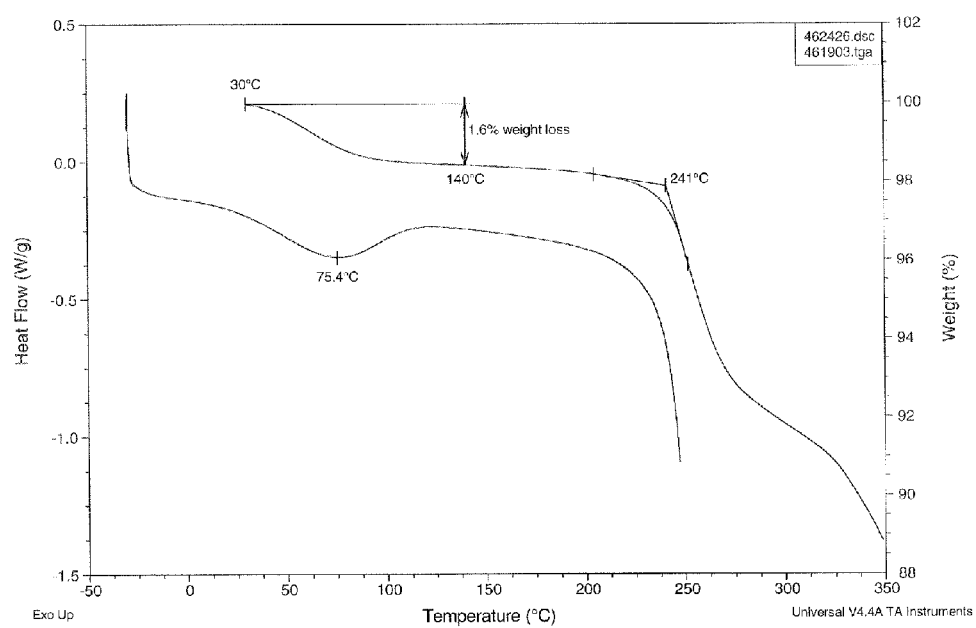
FIG. 6 shows DSC and TGA overlay of NI.H$_3$PO$_4$ Form C.

An overlay of the DSC and TGA thermograms for Form C is presented in FIG. 6. A broad endotherm at approximately 75° C. in the DSC thermogram corresponds with approximately 1.6% weight loss from 30 to 140° C. by TGA, indicating volatilization of solvent, likely water. A sharp decline in the TGA thermogram, with an onset marked at 241° C., indicates probable decomposition. No melting was observed by DSC as decomposition of the salt likely occurs prior to or concurrent with the melting.

Figure 7:
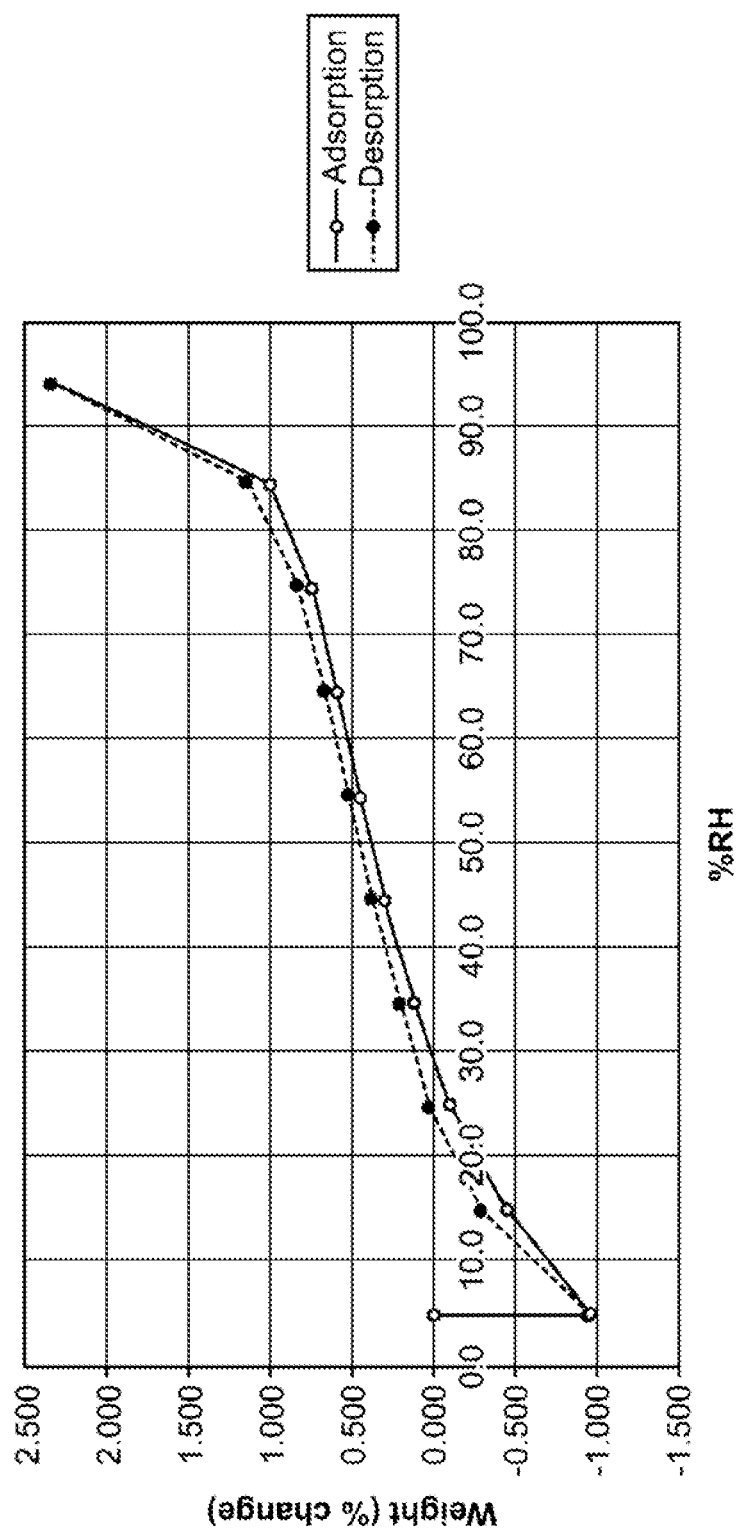
FIG. 7 shows DVS curves for NI.H$_3$PO$_4$ Form C.

The DVS curves for noribogaine phosphate (Form C) are shown in FIG. 7. Weight loss of approximately 1 wt % occurred upon equilibration to 5% RH, indicating loss of water that was present in the sample prior to the start of the experiment. Steady weight gain of approximately 3.3 wt % between 5 and 95% RH is observed; all of this weight was lost on desorption from 95 to 5% RH. XRPD of the post-DVS solids showed that the sample remained Form C after sorption/desorption.

Form D crystals were indexed as shown below.

| Bravais type | Primitive orthorhombic |
|---|---|
| a [Å] | 8.628 |
| b [Å] | 14.122 |
| c [Å] | 15.455 |
| α [deg] | 90 |
| β [deg] | 90 |
| γ [deg] | 90 |
| Volume [Å³/cell] | 1,883.1 |
| Chiral Contents? | Chiral |
| Extinction Symbol | P 21 21 21 |
| Space Group(s) | P 21 21 21 (19) |

Form F crystals were indexed as shown below. It is contemplated that the larger cell volume of Form F compared with Form A could possibly accommodate one or two molecules of water or an additional hydrochloride molecule.

| Bravais type | Primitive orthorhombic |
|---|---|
| a [Å] | 10.043 |
| b [Å] | 10.842 |
| c [Å] | 16.903 |
| α [deg] | 90 |
| β [deg] | 90 |
| γ [deg] | 90 |
| Volume [Å³/cell] | 1,840.5 |
| Chiral Contents? | Chiral |
| Extinction Symbol | P 21 21 21 |
| Space Group(s) | P 21 21 21 (19) |

Figure 8:
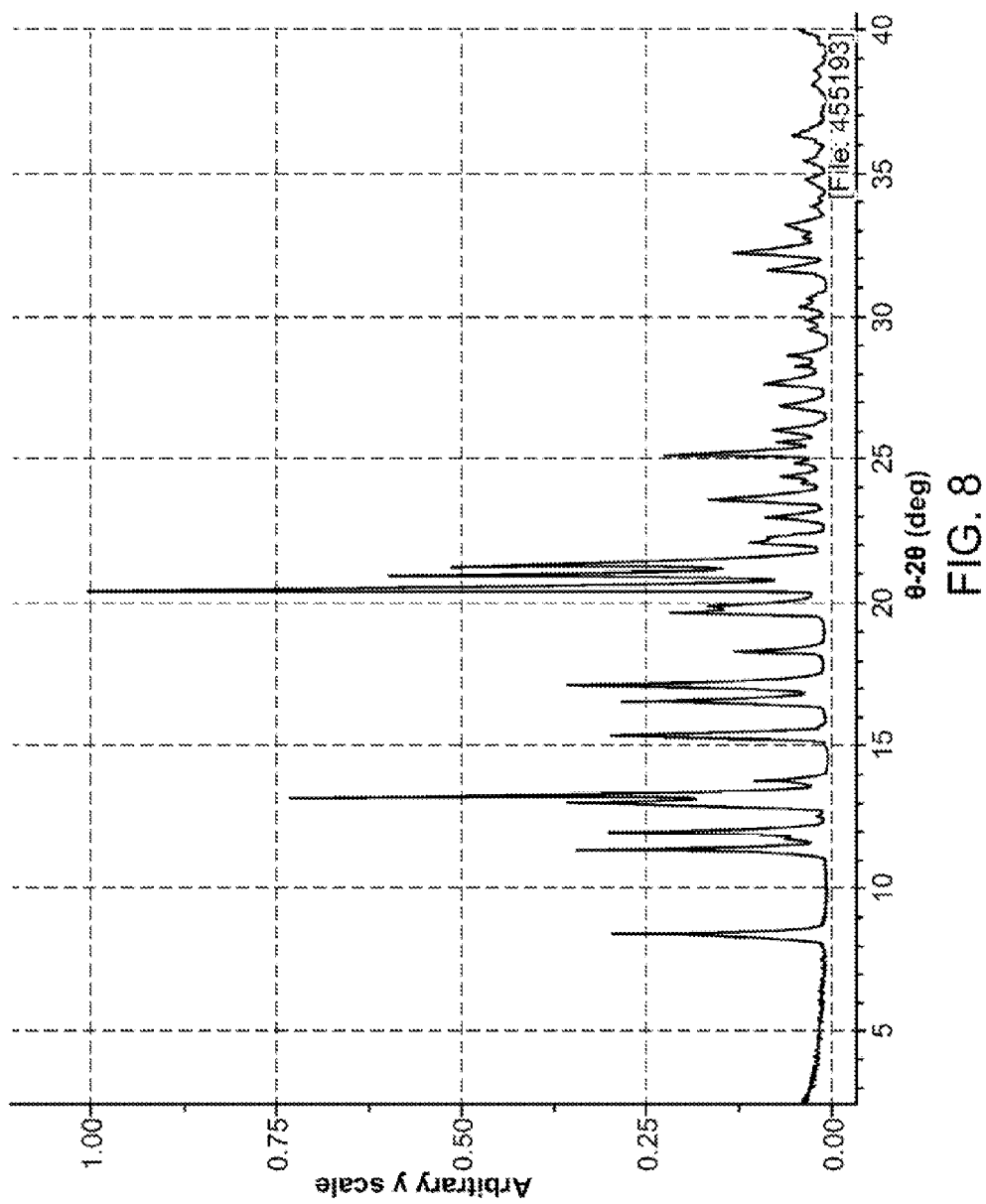
FIG. 8 shows the XRPD pattern of NI.H$_2$SO$_4$ Form D.
Figure 9:
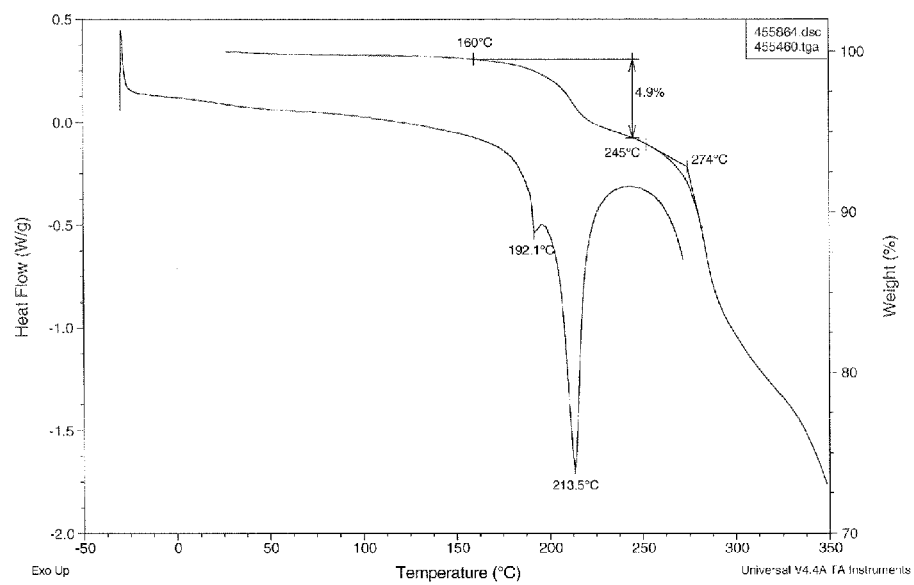
FIG. 9 shows DSC and TGA overlay of NI.H$_2$SO$_4$ Form D.

An overlay of the DSC and TGA thermograms for sulfate Form D is presented in FIG. 9. Weight loss of 4.9 wt % from approximately 160 to 245° C. by TGA corresponds with a small shoulder endotherm at approximately 192° C. overlapping a sharp endotherm at 214° C. by DSC, likely corresponding with simultaneous melting and dissociation of the salt (FIG. 8). The onset of likely decomposition is marked at approximately 274° C. in the TGA thermogram.

Figure 10:
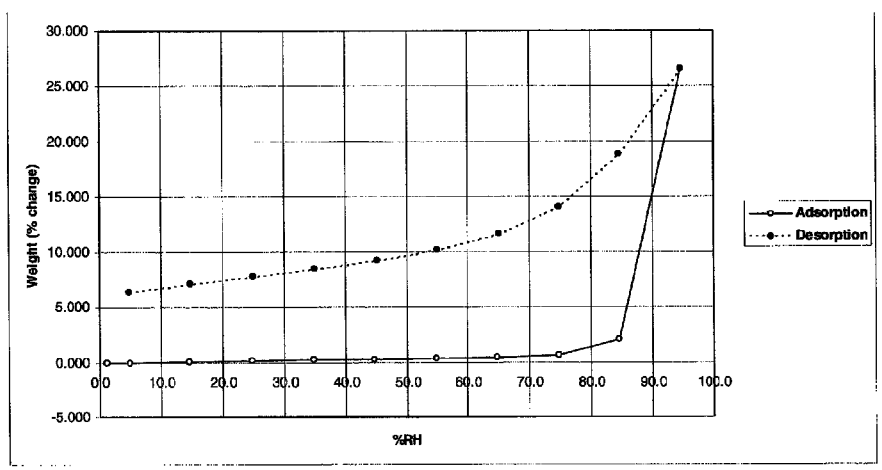
FIG. 10 shows DVS curves for NI.H$_2$SO$_4$ Form D.

The DVS curves for the sulfate salt are shown in FIG. 10. Relatively insignificant weight gain (about 0.7 wt %) was observed up to 75% RH, followed by approximately 26 wt % gain between 75 and 95% RH, indicating the material is very hygroscopic above 75% RH. The water gained was not completely lost on desorption from 95 to 5% RH. After analysis, the sample was observed to have deliquesced, consistent with the RH stressing experiments conducted previously.

Characterizing the Solids

Selected XRPD patterns were collected with an Inel XRG-3000 diffractometer. An incident beam of Cu Kα radiation was produced using a fine-focus tube and a parabolically graded multilayer mirror. Prior to the analysis, a silicon standard (NIST SRM 640c) was analyzed to verify the Si 111 peak position. A specimen of the sample was packed into a thin-walled glass capillary, and a beam-stop was used to minimize the background from air. Diffraction patterns were collected in transmission geometry using Windif v. 6.6 software and a curved position sensitive Equinox detector with a 2θ range of 120°.

Selected XRPD patterns were also collected with a PANalytical X'Pert PRO MPD diffractometer using an incident beam of Cu radiation produced using an Optix long, fine-focus source. An elliptically graded multilayer mirror was used to focus Cu Kα X-rays through the specimen and onto the detector. Prior to the analysis, a silicon specimen (NIST SRM 640d) was analyzed to verify the Si 111 peak position. A specimen of the sample was sandwiched between 3 µm thick films and analyzed in transmission geometry. A beam-stop, short antiscatter extension, and antiscatter knife edge (select samples only) were used to minimize the background generated by air. Soller slits for the incident and diffracted beams were used to minimize broadening from axial divergence. Diffraction patterns were collected using a scanning position-sensitive detector (X'Celerator) located 240 mm from the specimen and Data Collector software v. 2.2b.

DSC was performed using a TA Instruments Q2000 differential scanning calorimeter. Temperature calibration was performed using NIST traceable indium metal. The sample was placed into an aluminum DSC pan, covered with a lid, and the weight was accurately recorded. A weighed aluminum pan configured as the sample pan was placed on the reference side of the cell.

Thermogravimetric analyses were performed using a TA Instruments Q5000 IR thermogravimetric analyzer. Temperature calibration was performed using nickel and Alumel™ Each sample was placed in an aluminum pan. The sample was hermetically sealed, the lid pierced, then inserted into the TO furnace. The furnace was heated under nitrogen.

Dynamic vapor sorption (DVS) data were collected on a VTI SOA-100 Vapor Sorption Analyzer. NaCl and PVP were used as calibration standards. Samples were not dried prior to analysis. Sorption and desorption data were collected over a range from 5 to 95% RH at 10% RH increments under a nitrogen purge. The equilibrium criterion used for analysis was less than 0.0100% weight change in 5 minutes with a maximum equilibration time of 3 hours. Data were not corrected for the initial moisture content of the samples.

EXAMPLES

The following abbreviations are used in the examples and in this disclosure:
ACN acetonitrile
EtOH ethanol
EtOAc ethyl acetate
HFIPA hexafluoroisopropanol
MeOH methanol
MTBE tert-butyl methyl ether
TFE 2,2,2-trifluoroethanol
THF tetrahydrofuran
SC slow cool
SE slow evaporation
VD vapor diffusion
VS vapor stress
DSC differential scanning calorimetry
DVS Dynamic vapor sorption
XRPD x-ray powder diffraction
B/E birefringence with extinction
conc. concentrated
endo endotherm
P.O. preferred orientation
ppt. precipitation/precipitate
RH Relative humidity
RT room (ambient) temperature
TGA Thermogravimetric analysis

Example 1

Solubility of Form A Polymorph

The solubility of noribogaine hydrochloride ansolvate were determined as tabulated below.

TABLE 2

| Solvent System | Solubility (mg/mL)[a] |
|---|---|
| Acetone | <1 |
| Acetone:water 50:50 | 11 |
| CAN | <1 |
| ACN:water 80:20 | 9 |
| chloroform | <1 |
| chloroform:EtOH 50:50 | <1 |
| p-dioxane | <1 |
| EtOAc | <1 |
| EtOH | <1 |
| HFIPA | 10 |
| MeOH | 2 |
| MeOH:THF 50:50 | 1 |
| TFE | 4 |
| TFE:water 50:50 | 10 |
| THF | <1 |
| Water | <4 [b] |

[a] Solubilities were calculated based on the total solvent used to give a solution.
[b] Solubility measurement made by adding water all at once and allowing mixture to stir for ~24 hours, resulting in a clear solution with a very small amount of find solids in suspension.

Example 2

Preparation of Crystal Form A

Noribogaine hydrochloride ansolvate Form A was prepared by formation of the hydrochloride salt from the free base in IPA. Noribogaine free base (136 g) was charged to a 5 L flange flask fitted with a nitrogen inlet, gas bubbler, overhead stirrer, dropping funnel and thermometer. Isopropanol (3.27 L) was added and the mixture was heated under stirring and nitrogen atmosphere to 45-55° C. over one hour to afford a clear solution. Isopropanol/HCl (5 M, 128.6 ml, 1.4 eq). was added over one hour. Precipitation of an off-white solid was observed and the suspension was allowed to cool under stirring to room temperature overnight. The mixture was further chilled to 0-5° C. After 30 minutes the solid was collected by filtration and washed with DCM (2×0.49 L) and sucked dry to constant weight under nitrogen purge. The solid was further dried under vacuum at 60° C. for four days to afford. 150 g of Noribogaine hydrochloride which was shown to be Form A by XRPD.

Various solid forms of noribogaine obtained from various solvents are tabulated below

TABLE 3

| Solvent/Solvent System | Conditions | Habit/Description |
|---|---|---|
| acetone | dissolve free base w/ sonication | clear black solution |
|  | add conc. acid w/ stirring | ppt. on contact, opaque purple suspension |
|  | stir at RT, 1 day | opaque brownish-gray suspension; tiny particles and aggregates, B/E |
| IPA | dissolve free base w/ sonication | clear black solution |
|  | add conc. acid w/ stirring | ppt. formed, opaque dark brown suspension |
|  | stir at RT, 1 day | opaque purplish-gray suspension; very tiny particles and aggregates, partial B/E |
| MeOH | dissolve free base w/ sonication | clear black solution |
|  | add conc. acid w/ stirring | clear reddish-black solution |
|  | stir at RT, 1 day | cloudy brown suspension (solids present); after isolating - off-white, tiny particles, and aggregates, B/E |

TABLE 4

| Solvent/Solvent System | Conditions | Habit/Description |
|---|---|---|
| TFE | stir at ~68° C. for ~1.5 hrs., SC, | clear solution |
|  | ~68° C. to RT, stir at RT 1 day |  |
|  | refrigerator, 1 day | clear solution |
|  | mill, 30 Hz, 30 min. | white, tiny particles and aggregates, partial B/E |
| water | VS, ~41° C., 7 days | dry off-white solids, droplets of solvent on walls; rectangular plates, B/E |
|  | mill, 30 Hz, 30 min. | white, tiny particles and aggregates, partial B/E |
|  | slurry, ~38° C., 3 days | cloudy brown solution, off white solids; rectangular plates, B/E |
| IPA | slurry, ~39° C., 3 days | clear liquid phase, off white solids; rectangular plates, B/E |
| HFIPA | VD w/MTBE, 8 days | clear liquid phase, small amount white solids on bottom; aggregates and unknown morphology, partial B/E |

TABLE 4-continued

| Solvent/Solvent System | Conditions | Habit/Description |
|---|---|---|
| EtOH | slurry, ~39° C., 3 days | clear liquid phase, off white solids; rectangular plates, B/E |
|  | VS, ~41° C., 7 days | damp off-white solids; rectangular plates, B/E |
| ACN:water 90:10 | slurry, RT, 7 days | clear liquid phase, off white solids; rectangular plates, B/E |

Example 3

Preparation of Crystal Form C, the Phosphate Salt

Noribogaine free base (0.9055 g) was dissolved in IPA (20 mL) with sonication, yielding a clear, very dark green solution. Phosphoric acid (0.209 mL, concentrated) was added in a 1:1 stoichiometric ratio with stirring, causing precipitation on contact and resulting in an opaque gray suspension. The mixture was allowed to stir at ambient conditions for 3 days, at which time an opaque dark purple suspension was observed. Solids were collected by vacuum filtration, causing a color change from dark purple to light purplish-gray while the solids were air drying on the filter. The resulting solids were designated as a mixture of Form C (phosphate) and another Form, E, by XRPD. A portion of the solids (0.6009 g) was added to an 80:20 mixture of EtOH and water (total of 2 mL), and undissolved solids remained. The slurry was loaded onto an orbital shaker and was agitated at ambient temperature and 150 rpm for 3 days, affording an opaque purplish-gray suspension. The solids were collected by vacuum filtration and vacuum dried at ambient temperature for 1 day, resulting in pure Form C (phosphate) by XRPD.

Example 4

Preparation of Crystal Form D, the Sulfate Salt

Noribogaine free base (0.7730 g) was dissolved in IPA (25 mL) with sonication, resulting in a clear green solution. Concentrated sulfuric acid (0.1463 mL) was added in a 1:1 molar ratio with stirring, causing precipitation on contact, giving an opaque very light gray suspension. The mixture was allowed to stir at ambient conditions for 3 days, and the solids were collected by vacuum filtration and washed with IPA (89% yield).

Example 5

Preparation of Crystal Form F of the Hydrochloride Salt

Form F was prepared by precipitation of the HCl salt from a MeOH solution of the free base by adding methanolic HCl and subsequently purifying by slurrying in MeOH. Form F was characterized by XRPD as shown in the middle panel of FIG. 4.

Example 5

Conversion of Form F to Pure Form A Ansolvate

Surprisingly, it was observed that the solvated polymorph F, converted to the ansolvate form A, upon stirring in 9:1 ethyl alcohol and water. Such a desolvation is surprising, given that it occurs upon stirring in another solvent, which comprises hydroxy groups and alkyl moieties as in MeOH. As described above, form F is a solvated polymorph that is obtained from MeOH. The form F polymorph also converts to the ansolvate form A upon heating.

Example 7

Preparation of Crystal form G of the Hydrochloride Salt

Figure 4:
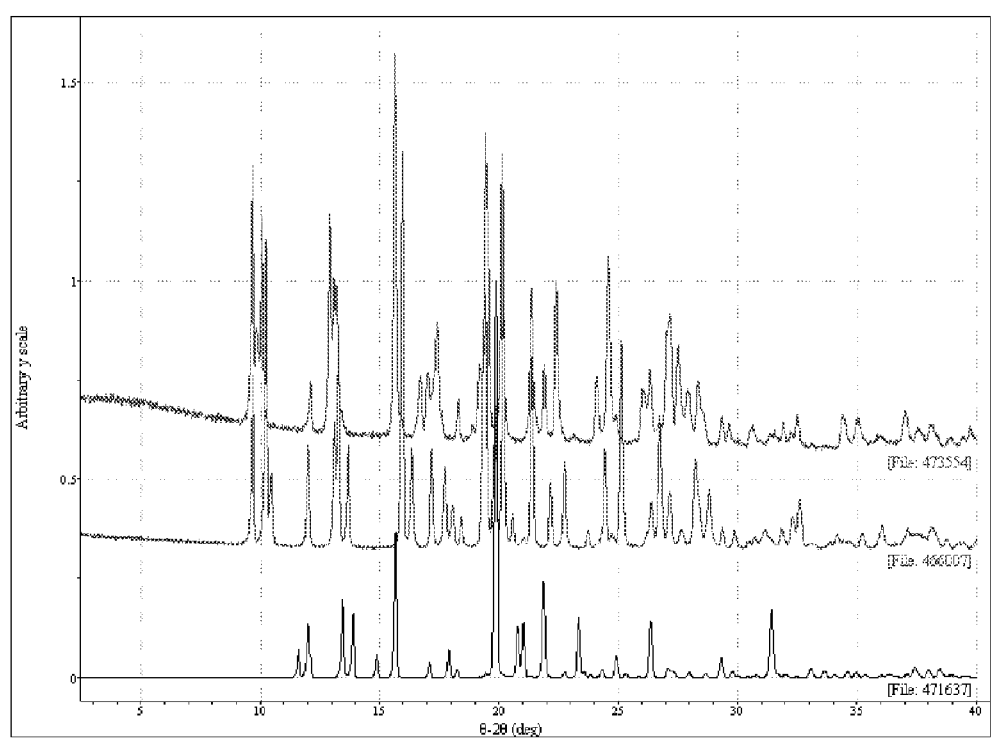
FIG. 4 shows, in the top panel, an XRPD pattern of the noribogaine hydrochloride Form G obtained when a methanol slurry of noribogaine hydrochloride Form A was kept at room temperature for 7 days, in the middle panel, an XRPD pattern of Form F, and in the bottom panel, an XRPD pattern of noribogaine hydrochloride ansolvate Form A.

When a methanol slurry of noribogaine hydrochloride was kept at room temperature for 7 days, off white, rectangular aggregates and irregular plates were obtained (Form G), which showed XRPD as shown in the top panel of FIG. 4.

Figure 3:
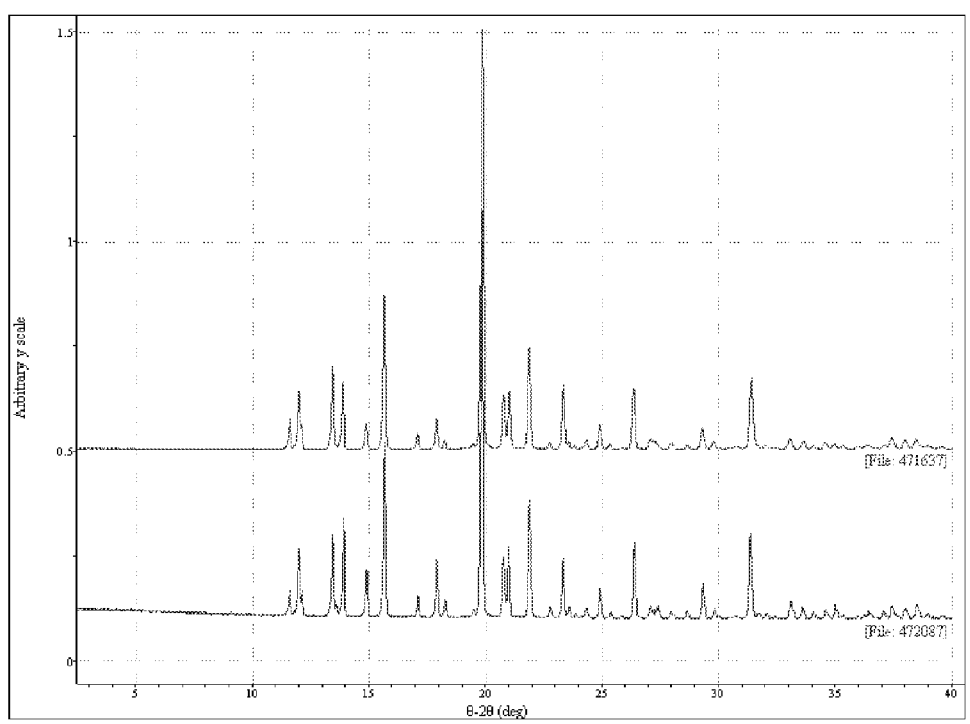
FIG. 3 shows X-ray powder diffraction (XRPD) patterns of two samples of noribogaine hydrochloride ansolvate Form A.
Figure 5:
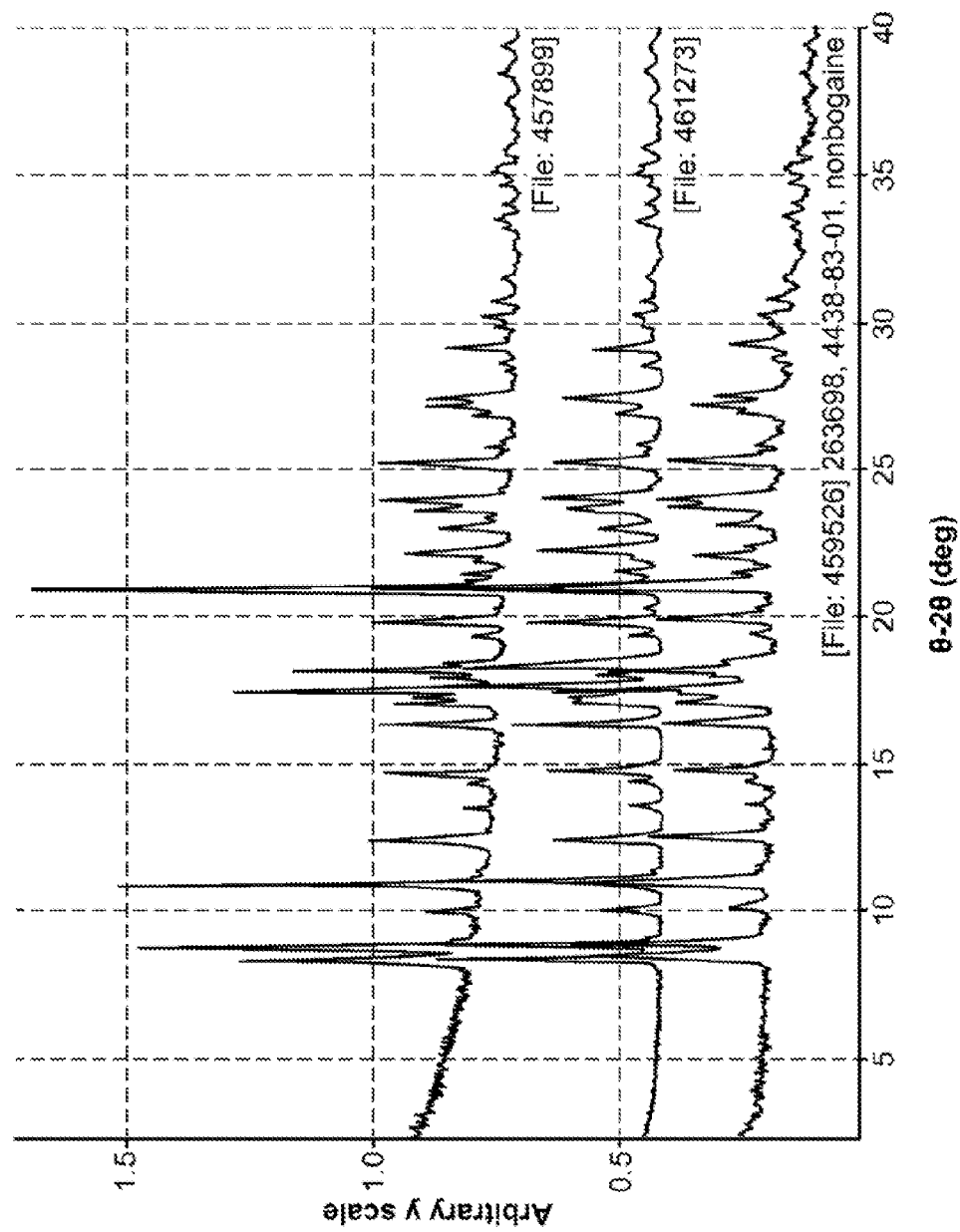
FIG. 5 shows XRPD overlay of NI.H$_3$PO$_4$ Form C with minor peak shifting.

The invention claimed is:

1. A method of treating a patient to alleviate nociceptive pain in the absence of a treatment of drug dependence or drug abuse and in the absence of any concomitant opioid analgesic therapy, comprising: administering systemically to said patient a pharmaceutical composition comprising an effective-amount of a noribogaine salt selected from:

a pharmaceutically acceptable salt of noribogaine ansolvate, which is amorphous or is a crystalline hydrochloride salt having an X-ray powder diffraction pattern comprising peaks at 11.6±0.2° 2θ, 12.1±0.2° 2θ, 13.5±0.2° 2θ, 13.9±0.2° 2θ, 14.9±0.2° 2θ, 15.7±0.2° 2θ, 17.1±0.2° 2θ, 17.9±0.2° 2θ, 18.3±0.2° 2θ, 19.8±0.2° 2θ, 20.8±0.2°, 21.0±0.2° 2θ, 21.9±0.2° 2θ, 22.8±0.2° 2θ, 23.3±0.2° 2θ, 24.9±0.2° 2θ, 25.9±0.2°, 26.4±0.2° 2θ, 29.3±0.2° 2θ and 29.8±0.2° 2θ as shown in FIG. 3; or is a crystalline sulfate salt having an X-ray powder diffraction pattern comprising peaks at 8.5±0.2° 2θ, 11.4±0.2° 2θ, 12.0±0.2° 2θ, 13.3±0.2° 2θ, 15.4±0.2° 2θ, 16.6±0.2°, 17.2±0.2° 2θ, 18.3±0.2° 2θ, 20.6±0.2° 2θ, 21.0±0.2° 2θ and 21.5±0.2° 2θ as shown in FIG. 8; when analyzed using CuKα X-ray radiation;

a crystalline noribogaine hydrochloride solvate polymorph having an X-ray powder diffraction pattern comprising peaks at 9.7±0.2° 2θ, 10.2±0.2° 2θ, 12.0±0.2° 2θ, 13.3±0.2° 2θ, 13.7±0.2° 2θ, 16.0±0.2° 2θ, 16.3±0.2° 2θ, 17.7±0.2° 2θ, 18.0±0.2° 2θ, 19.4±0.2° 2θ, 21.4±0.2° 2θ, 22.1±0.2° 2θ, 22.8±0.2° 2θ, 24.4±0.2° 2θ and 25.1±0.2° 2θ as shown in FIG. 4, when analyzed using CuKα X-ray radiation; and a crystalline polymorph of a phosphate salt of noribogaine, having an X-ray powder diffraction pattern comprising peaks as shown in FIG. 5, When analyzed using CuKα X-ray radiation;

to said patient effective to reduce or eliminate said nociceptive pain in said patient.

2. The method of claim 1, wherein the noribogaine salt has an X-ray powder diffraction pattern comprising peaks at 11.6±0.2° 2θ, 12.1±0.2° 2θ, 13.5±0.2° 2θ, 13.9±0.2° 2θ, 14.9±0.2°, 15.7±0.2' 2θ, 17.1±0.2° 2θ, 17.9±0.2° 2θ, 18.3±0.2° 2θ, 19.8±0.2° 2θ, 20.8±0.2°, 2θ, 21.0±0.2° 2θ, 21.9±0.2° 2θ, 22.8±0.2° 2θ, 23.3±0.2° 2θ, 24.9±0.2° 2θ, 25.9±0.2°, 26.4±0.2° 2θ, 29.3±0.2° 2θ and 29.8±0.2° 2θ as shown in FIG. 3, when analyzed using CuKα X-ray radiation.

3. The method of claim 1, wherein the noribogaine salt has an X-ray powder diffraction pattern comprising peaks at 9.7±0.2° 2θ, 10.2±0.2° 2θ, 12.0±0.2° 2θ, 13.3±0.2° 2θ, 13.7±0.2° 2θ, 16.0±0.2° 2θ, 16.3±0.2° 2θ, 17.7±0.2° 2θ, 18.0±0.2° 2θ, 19.4±0.2° 2θ, 21.4±0.2° 2θ, 22.1±0.2° 2θ, 22.8±0.2° 2θ, 24.4±0.2° 2θ and 25.1±0.2° 2θ as shown in FIG. 4, when analyzed using CuKα X-ray radiation.

4. The method of claim 1, wherein the noribogaine salt has an X-ray powder diffraction pattern comprising peaks at 8.5±0.2° 2θ, 11.4±0.2° 2θ, 12.0±0.2° 2θ, 13.3±0.2° 2θ, 15.4±0.2° 2θ, 16.6±0.2° 2θ, 17.2±0.2° 2θ, 18.3±0.2° 2θ, 20.6±0.2° 2θ, 21.0±0.2° 2θ and 21.5±0.2° 2θ as shown in FIG. 8, when analyzed using CuKα X-ray radiation.

5. The method of claim 1, wherein the noribogaine salt is a phosphate salt of noribogaine, having an X-ray powder diffraction pattern comprising peaks as shown in FIG. 5, when analyzed using CuKα X-ray radiation.

* * * * *